United States Patent
Miyazaki et al.

(10) Patent No.: US 6,656,115 B1
(45) Date of Patent: Dec. 2, 2003

(54) MEDICAL INFORMATION SYSTEM

(75) Inventors: Jinsei Miyazaki, Higashiosaka (JP); Kenji Iwano, Nara (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 136 days.

(21) Appl. No.: 09/653,814

(22) Filed: Sep. 1, 2000

(30) Foreign Application Priority Data

Mar. 31, 2000 (JP) ..................... 2000-097301

(51) Int. Cl.[7] ............................... A61B 5/00
(52) U.S. Cl. .......................... 600/300; 128/904
(58) Field of Search ................. 600/300, 301; 128/903, 904; 482/1, 8, 901

(56) References Cited

U.S. PATENT DOCUMENTS

| | | | |
|---|---|---|---|
| 4,974,607 A | * 12/1990 | Miwa | .................. 128/903 |
| 5,550,902 A | 8/1996 | Abbruscato | |
| 5,857,967 A | 1/1999 | Frid et al. | |
| 5,865,745 A | 2/1999 | Schmitt et al. | |
| 5,868,135 A | * 2/1999 | Kaufman et al. | .......... 600/300 |
| 5,899,855 A | 5/1999 | Brown | |
| 5,954,641 A | * 9/1999 | Kehr et al. | ............... 600/300 |
| 5,967,975 A | * 10/1999 | Ridgeway | ................. 600/300 |
| 6,024,699 A | * 2/2000 | Surwit et al. | ............... 600/300 |
| 6,139,494 A | * 10/2000 | Cairnes | ..................... 600/300 |
| 6,171,237 B1 | * 1/2001 | Avitall et al. | .............. 600/300 |
| 6,198,394 B1 | * 3/2001 | Jacobsen et al. | ........... 600/301 |
| 6,398,727 B1 | * 6/2002 | Bui et al. | ................... 600/300 |
| 6,416,471 B1 | * 7/2002 | Kumar et al. | .............. 128/903 |

FOREIGN PATENT DOCUMENTS

| | | |
|---|---|---|
| JP | 7-116128 | 9/1995 |
| JP | 9-253058 | 9/1997 |
| JP | 10-261035 | 9/1998 |
| JP | 2000-57216 | 2/2000 |

* cited by examiner

*Primary Examiner*—Eric F. Winakur
*Assistant Examiner*—David J. McCrosky
(74) *Attorney, Agent, or Firm*—RatnerPrestia

(57) ABSTRACT

A medical information system has a patient terminal device, a server, and an administrator terminal device. The patient terminal device, the server, and the administrator terminal device are connected together on a network. The patient terminal device includes sensors for measuring information used as indices of the condition of a patient's health; a part for transferring measured data obtained by the sensors to the patient terminal device; a part for transferring the measured data from the sensors to the server via the network; a part for accepting control information from the server, and a part for taking action based on the control information. The server includes a part for transmitting the control information to the patient terminal device; and a part for storing and sorting out the measured data transferred from the patient terminal device. The administrator terminal includes a part for reviewing the measured data stored and sorted out in the server.

16 Claims, 1 Drawing Sheet

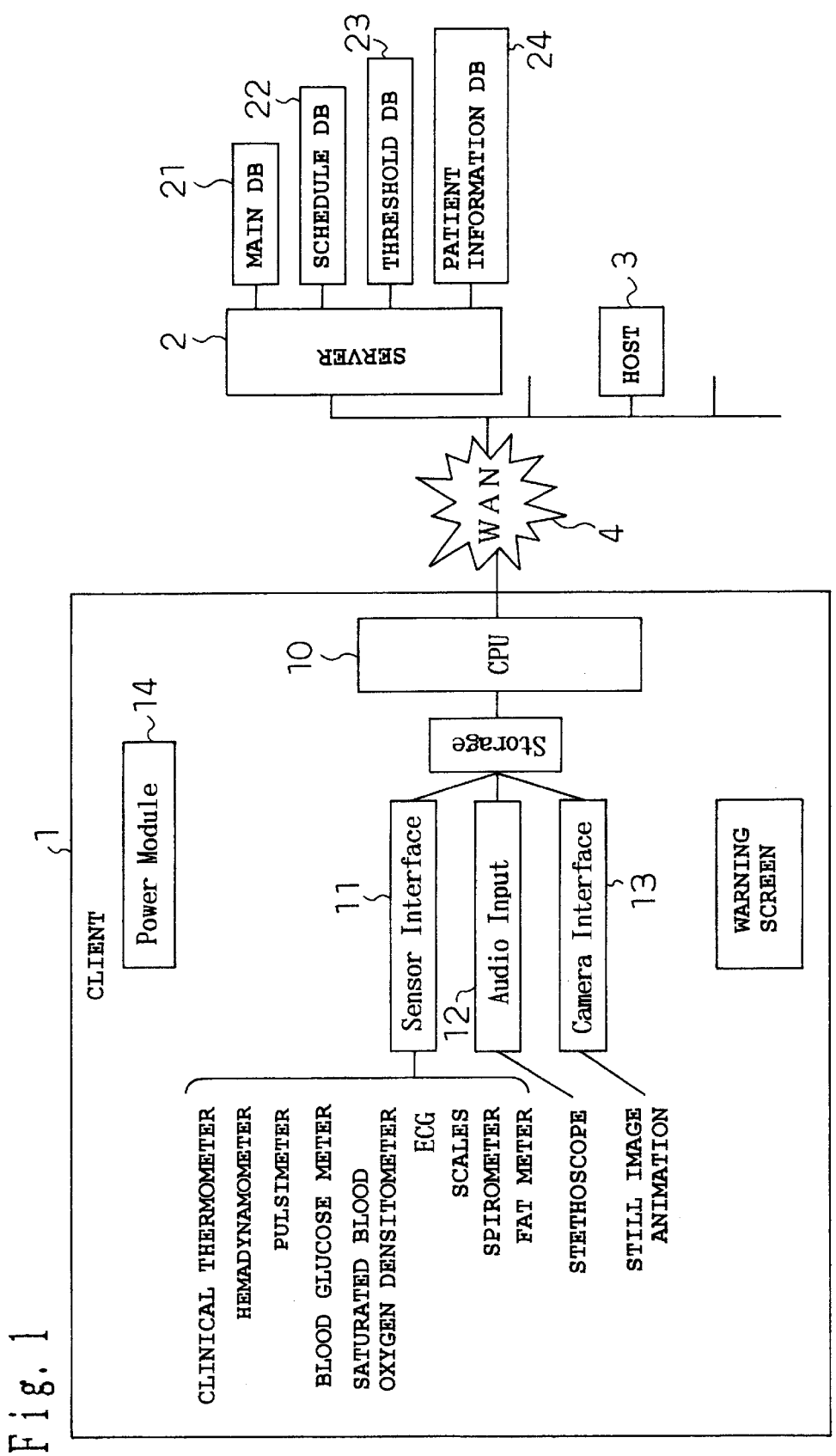

MEDICAL INFORMATION SYSTEM

BACKGROUND OF THE INVENTION

1. Field of the Invention

The present invention relates to a remote medical technology for transmitting data between a practitioner and a remote patient by using a network.

2. Description of the Related Art

Despite an increased lifetime expectancy resulting from improved medical technologies, what is called aging of society, that is, an increase in the ratio of the number of aged people to the population, becomes a global problem. In the aging society, the incidence of chronic diseases such as diabetes, heart diseases, and rheumatism increases necessarily. It is a great burden or pain on patients with chronic diseases to go to hospital for a long period of time, while practitioners must spend too long a time in treating such patients to undertake more critical treatments.

In these circumstances, remote medical systems using computer communications have been proposed. In a typical example, a patient terminal comprises a computer having sensors such as a clinical thermometer and a hemadynamometer connected thereto to communicate a remote computer possessed by a practitioner. Thus, the patient can make basic measurements at home without going to hospital and is required to visit the practitioner only if the patient must truly be treated, thereby reducing the burdens on both patient and practitioner.

However, the number of chronic-disease patients to be treated by one practitioner has been increasing rapidly, so that the above described on-to-one communications do not necessarily improve any substantial medical efficiency in that the practitioner must spend an amount of time treating each patient.

In view of these conventional situation, it is an object of the present invention to provide a medical information system that can-improve the medical efficiency without making any burden for the practitioner.

SUMMARY OF THE INVENTION

One aspect of the present invention is a medical information system, comprising a patient terminal device, a server, and an administrator terminal device, characterized in that:

said patient terminal device, said server, and said administrator terminal device are connected together on a network;

said patient terminal device includes sensors having functions for measuring information used as indices of the condition of a patient's health; means for transferring measured data obtained by said sensors to an interior of said patient terminal device; means for transferring said measured data from said sensors to said server via the network; and means for accepting control information from said server, and has a function of taking action based on said control information;

said server includes means for transmitting the control information to said patient terminal device; and means for storing and sorting out said measured data transferred from said patient terminal device; and said administrator terminal includes means for viewing said measured data stored and sorted out in said server.

Another aspect of the present invention is the medical information system, characterized in that said server has a function for managing information unique to a user using said patient terminal device and can supply individual data or individual control information to, said patient terminal device based on the information unique to said user.

Still another aspect of the present invention is the medical information system, characterized in that said sensors comprises at least one of a clinical thermometer, a hemadynamometer, a pulsimeter, a blood sugar level meter, a saturated blood oxygen densitometer, scales, a fat meter, a stethoscope, an electrocardiograph, a still image pickup device, an animation image pickup device, and a spirometer.

Yet still another aspect of the present invention is the medical information system, characterized in that said server possesses predetermined schedule information for individual patients and transmits a request to said patient terminal device in accordance with the schedule information, said patient terminal device takes action depending on the request.

Still yet another aspect of the present invention is the medical information system, characterized in that said server compares said schedule information with measured data transferred from said patient terminal device in terms of time to change said schedule.

A further aspect of the present invention is the medical information system, characterized in that if the measured data is transmitted from the patient terminal ahead of a scheduled time and the difference in time is within an allowable range, said server changes the schedule to avoid said request corresponding to the measured data.

A still further aspect of the present invention is the medical information system, characterized in that if the measured data is transmitted from said sensors before said request has been transmitted and the difference in time between a measuring time and said subsequently transmitted corresponding request is within an allowable range, said patient terminal device does not take action depending on the request.

A yet further aspect of the present invention is the medical information system, characterized in that said patient terminal device possesses schedule information on the patient transmitted from said server, to take action in accordance with the schedule information.

A still yet further aspect of the present invention is the medical information system, characterized in that said patient terminal device compares said schedule information with the measured data transferred from said sensors in terms of time to change said schedule.

An additional aspect of the present invention is the medical information system, characterized in that if the measured data is transmitted to the patient terminal device ahead of a scheduled time and the difference in time is within an allowable range, said patient terminal device changes the schedule to avoid said action corresponding to the measured data.

A still additional aspect of the present invention is the medical information system, characterized in that in the case when said patient terminal device does not receive measured data from the sensors within a predetermined time after taking action, it takes action for warning that the patient has forgotten to make measurements.

A yet additional aspect of the present invention is the medical information system, characterized in that said server possesses threshold values for data that depend on the condition of each patient's health and has a function for transmitting a signal to said administrator terminal device via a network in the case when the measured data transferred from said patient terminal device deviate from said threshold values.

A still yet additional aspect of the present invention is the medical information system, characterized in that said patient terminal device possesses threshold values for data that depend on the condition of each patient's health and has a function for transmitting a signal to said administrator terminal device via a network in the case when the measured data transferred from said patient terminal device deviate from said threshold values.

A supplementary aspect of the present invention is the medical information system, characterized in that said server stores at least part of software driving said patient terminal device or/and said administrator terminal device has a function operating when said software is updated, to automatically update said software in said patient terminal device or/and said administrator.

BRIEF DESCRIPTION OF THE DRAWINGS

FIG. 1 is a schematic view showing the configuration of a network for a medical information system according to one embodiment of the present invention.

DESCRIPTION OF SYMBOLS

1 Client
2 Server
3 Host
4 WAN
10 CPU
21 Main DB
22 Schedule DB
23 Threshold DB
24 Patient information DB

DESCRIPTION OF THE PREFERRED EMBODIMENTS

An embodiment of the present invention will be described below. A medical information system according to the present invention comprises a patient terminal device (hereafter referred to as a "client"), a server (hereafter referred to as a "server"), and an administrator terminal device (hereafter referred to as a "host"), which are connected together on a network.

The client has sensors having functions for measuring information used as indices of the condition of a patient's health, means for transferring measured data obtained by the sensors to an interior of the client, means for transferring the measured data from the sensors to the server via the network, and means for accepting control information from the server. The client also has a function for taking action based on the control information.

The server has means for storing and sorting out the measured data transferred from the client, while the host has a function for viewing the measured data stored and sorted out in the server.

In the medical information system according to the present invention, the server is not a simple site to which data are stored but constitutes a system acting as a center in taking action. The server can request the client to take action such as turning-on or -off of a sleep state of the client terminal, a data transfer command, and a measurement indication.

To realize these operations, all information may be placed only in the server, which transmits control signals from the server. Alternatively, the control information is stored in the client so that the client can solely carry out the above described control. The control information, however, is also stored in the server, and management of the information such as listing or changed is executed on the server.

For data from the sensors, threshold values are stored on the server for each patient so that when data are transferred to the server, the server can compare the current data with the threshold values to find errors in order to determine action must be taken. The server take actions such as warning against the host or the client.

Alternatively, the threshold information for each patient which is managed on the server is transferred to the client beforehand so that the client can compare this information with the data to take action such as a warning to the client, the server, or the host.

Embodiment 1

Embodiment 1 of the present invention will be explained in detail below with reference to FIG. 1. This figure is a schematic view showing the configuration of a network for a medical information system according to one embodiment of the present invention. A client 1 has an 1) interface 11 for transferring data from sensors such as a clinical thermometer, a hemadynamometer, a sphygmograph, a blood glucose meter, a saturated blood oxygen densitometer, an electrocardiograph, and a spirometer to a CPU 10, an 2) analog sound signal input interface 12 having a stethoscope connected thereto, an 3) interface 13 having an electronic camera for still images connected thereto, and an 4) interface 13 having a video camera for animations (desirably a digital video camera) connected thereto.

According to this embodiment, however, data from the scales and the spirometer, which are displayed on these sensors, are manually read and input on the computer in order to reduce costs and because these sensors do not necessarily require automatic inputs.

Additionally, a power module 14 can turn on or off a power supply to the client 1 in response to a signal from the server 2. Motherboard in recently commercially available computers generally have a function called Wake On Call that operates if no operation has been performed for a fixed period of time after power-on, to enter a mode where the CPU 10 is driven at a low speed to power down a hard disc, a display, and other peripheral devices in order to reduce power consumption, that is, to enter a sleep state and then to clear this state to return to regular operations on receiving a signal from a modem or a LAN.

According to the present invention, the Wake On Call is treated as a kind of operation for turning on or off the power supply. In fact, the Wake On Call can reduce the costs of the main body more sharply than the use of the power module 14 for complete turn-on and -off operations. It can also reduce the time required for recovery. Thus, this embodiment uses the Wake On Call function.

The server 2 also has a 1) main database 21 that stores all data from the patient, a 2) schedule database 22 that stores schedules for temporal actions, a 3) threshold database 23 that stores threshold values for the data, and a 4) patient information database 24 that stores patient's personal information, which are all managed by so-called database software.

Next, the databases (hereafter simply referred to as "DBs"), on which operations are based, will be described. First, the schedule DB22 is shown in (Table 1).

TABLE 1

| Patient | Patient A | Patient B | ... |
|---|---|---|---|
| Power-on | 7:00 | 8:00 | |
| Power-off | 20:30 | 22:00 | |
| Temperature | 8:00, 13:00 | 8:10 | |
| Blood pressure | 8:00, 13:00 | 14:00 | |
| Pulse rate | | | |
| Oxygen concentration | | 14:00, 19:00 | |
| Blood sugar level | 8:00, 13:00, 20:00 | | |
| ECG | | 15:00 | |
| Weight | | 14:00 | |
| Fat | | 14:00 | |
| Stethoscope | 13:00 | | |
| Image | 16:00 | | |
| Data transfer | OEM | OSD | |

One file contains schedules for all patients. More specifically, the horizontal axis indicates patient names or client identification numbers, while the vertical axis indicates all action items. Each section shows a point of time at which the action is taken for the patient, but the number of data in each section is not necessarily one but may vary depending the section. For example, a patient A must have his or her temperature measured at 8:00 and 13:00, so that the two points of time are described in the corresponding section by inserting a comma therebetween.

Next, the main DB 21 (the patient A's data of Dec. 1, 2000) is shown in (Table 2).

TABLE 2

| Time data were obtained | 200012010802 | 200012011302 | 200012011602 | 200012012002 |
|---|---|---|---|---|
| Temperature | 36.6 | 36.5 | | |
| Blood pressure (maximum) | 185 | 190 | | |
| Blood pressure (minimum) | 125 | 128 | | |
| Pulse rate | 68.5 | 71.5 | | |
| Oxygen concentration | | | | |
| Blood sugar level | 205.2 | 125.8 | | 115.0 |
| ECG | | | | |
| Weight | | | | |
| Fat | | | | |
| Stethoscope | S12010802AB | | | |
| Image | C12010802AB | | | |

One file is provided for each patient or each date. The horizontal axis indicates the points of time when the data were obtained, while the vertical axis indicates each data item. The data are essentially described in a text format but the stethoscope data is an audio file and is so large that only the file name is described. The ECG data and the image are also so large that only their file names are described. The first character of the description identifies the type of data; that is, S indicates a stethoscope, C indicates images, and E indicates ECG (is not contained in the data sections in this embodiment). The subsequent number indicates a date and a point of time, and the two final characters are the patient's ID.

Naturally enough, the main DB 21 has a large file configuration. Accordingly, an optimal configuration method may vary depending on the system configuration or database software used. In short, it is important to efficiently store the patient names or client ID numbers, the times when the data were obtained, the data types, and the data contents.

Next, the threshold DB23 is shown in (Table 3).

TABLE 3

| | Patient A | Patient B | Patient C | Patient X |
|---|---|---|---|---|
| Temperature | 37.0 | 38.0 | 38.0 | 38.0 |
| Blood pressure (maximum) | x | 150 | 150 | 150 |
| Blood pressure (minimum) | x | 60 | 60 | 60 |
| Pulse rate (maximum) | 150 | 120 | 120 | 120 |
| Pulse rate (minimum) | x | x | x | x |
| Oxygen concentration | 90 | 85 | 90 | 90 |
| Blood sugar level | 200 | 120 | 120 | 120 |
| Weight | D1000 | U70.0 | L48.5 | D1000 |
| Fat | 40 | 35 | 35 | 35 |

A threshold value of each measured item is described for each patient. For example, the patient A is abnormal if his or her temperature exceeds 37.0°, but a patient B is normal until his or her temperature exceeds 38.0°. In the table, Xs are shown in several sections, meaning that, for example, the blood pressure abnormal value is not monitored for the patient A.

These descriptions are provided because too many abnormal values may complicate corresponding actions to cause more critical abnormal values to be missed. For similar reasons, since, a general abnormal value of, for example, the blood sugar level is well known, this value may be applied to all the patients. A diabetes patient, however, constantly shows an abnormal value, so that a rapid change in this patient may be missed. To prevent this, threshold values for each patient are still important. Three types of descriptions are found in the weight section. The patient B is shown with U70.0, which means that the patient B is abnormal when his or her weight exceeds 70.0 kg. Likewise, a patient C is shown with L48.5, which means that 48.5 kg or lower is an abnormal value. Additionally, D1000, described for the patient A, means that the patient is abnormal when the difference between the current and preceding measured values is 1,000 g.

A specific operation of the medical information system configured as described above will be described taking the patient A by way of example.

Although the client 1 is basically powered all day long, it is not used at night and thus automatically sleeps during this period of time.

First, at 7 o'clock, the schedule DB 22 on the server 2 detects a power-on state. The server 2 uses the patient information DB24 to extract a telephone number of the client device 1 used by the patient A, and makes a call to this number. When the call is transmitted to the client 1 possessed by the patient A, the client 1 uses the Wake On Call function to leave the sleep state to start a normal operation.

At 8 o'clock, the server 2 detects that the patient A must measure his or her temperature, bloodpressure, and blood sugar level. The server 2 uses the patient information DB24 to extract the telephone number of the client device 1 used by the patient A, makes a call to this number to establish a network connection, and then displays a message on a screen of the client, prompting the patient to make measurements.

The message displayed is, for example, "Measurement Time. Measure Temperature, Blood Pressure, and Blood Sugar Level".

In addition, the patient is prompted to measure the temperature, blood pressure, and blood sugar level and allow a stethoscope measurement to be measured at 13:00, to photograph an image at 16:00, and to measure the blood sugar level in a similar manner at 20:00.

The pulse rate section of the scheduling DB22 in this embodiment is empty, but since typical hemadynamometers and oxygen densitometers also measure the pulse rate, the pulse rate is automatically measured when the blood pressure or the oxygen concentration is measured even if a point of time is not specified.

Similarly, after power-on is detected at 8 o'clock, the patient B is prompted to measure the temperature at 8:10, measure the blood pressure, oxygen concentration, weight, and fat at 14:00, measure the ECG at 15:00, and measure the oxygen concentration at 19:00.

The data measured as described above are, first of all, recorded in a storage device (in this case, a hard disc) in the main body of the clients. Subsequently, the data are transferred using timings corresponding to settings on the server 2. These timings are described in the data transfer section of the scheduling DB22. As shown in Table 1, possible contents of the descriptions include a transfer each time measurements are made (OEM: On Every Measurement), a transfer at the end of the day (OSD: On Shut Down), or a time specification (in this case, for example, fifteen twenty-five is 15:25).

Since the patient A is shown with the OEM description, data are transferred whenever the measurements are made. This method is characterized in that the practitioner can determine the patient's condition with the smallest temporal delay but is unsuitable for a system with a larger number of clients integrated therewith because the line is disadvantageously occupied for a long period of time.

On the other hand, the patient B is shown with the OSD description. In this case, when the server delivers a power-off signal to the client at 22:00, the client transfers all the data for the day and then enters an off state (in this case, the client sleeps). The advantages and disadvantages of this method are opposite to those of the OEM; since all the data are delivered with a single connection, latency required to establish the network is shortened to save the period of time that the network is occupied. On the contrary, the practitioner reads data delayed by 12 hours at maximum.

A compromise between these methods is to set transfer times for each patient, but this method requires cumbersome settings and management and is thus not employed for this embodiment.

Once the data have been transferred as described above, they are registered in the main database 21. For example, the patient A's data of Dec. 1, 2000 indicate that the temperature, blood pressure, pulse rate, blood sugar level, and stethoscope data were recorded at 8:02 (the top row shows an acceptance date and time in the order of year, month, day, and time. That is to say, in this case, 200012010802 is shown.)

The scheduled measuring time is 8:00, while the actual measuring time is 8:02; that is, there is a difference of two minutes between these times. More specifically, when each data is obtained, a header section there includes information on the measuring time. Thus, even if the data transfer is set for the OSD, the accurate measuring time is recorded.

Here, the server 2 compares the data measuring time with the descriptions in the scheduling DB to determine whether or not the scheduled measurements have been made. When a fixed period of time (in this embodiment, 30 minutes) has passed after the scheduled time, the server 2 transmits another type of alarm signal to the client 1, and the client 1 displays a more precise alarm message with an unpleasant beep sound instead of a simple prompt message.

On the contrary, patients who have much experience in measurements understand that their measurement time is about 8:00, and may make measurements at 7:55. If the patient make measurements ahead of the schedule, results of the measurements are considered to be formal, for example, if the difference in time is equal to or shorter than 10 minutes, that is, an allowable value. That is, the patient is not warned of the scheduled measurements at 8:00 and the subsequent warnings are avoided. That is, the server 2 changes the schedule. On the contrary, if the measurements are made more than 10 minutes ahead of the schedule, for example, at 7:30 in the above example, these measurement data are ignored and the patient is warned of the scheduled measurements at 8:00. That is, the schedule is not changed.

Alternatively, the server 2 may not carry out such a process but the client 1 may compare the request transmitted from the server 2 based on the schedule with the results of measurements from the sensors to determine whether the difference in time is smaller than the allowable value. If the difference is smaller than the allowable value, the data are considered to be formal. If the difference is larger than the allowable value, the data are neglected.

The server 2 can compare the data transferred as described above with the descriptions in the threshold DB24. For example, the patient A obtained a blood sugar level of 205 at 8:02 on Dec. 1, 2000, which value exceeds a threshold of 200 specified for this patient. On detecting this, the sensor 2 can take various actions.

In this case, when such data from the server 2 are viewed on the host 3, the characters are displayed with red. Thus, until the practitioner uses the host 3 to view the data, abnormal values are not found.

Accordingly, to communicate information in more real time, an electronic mail may be automatically transmitted, for example, to an information terminal carried by the practitioner, the mail stating that, for example, "patient A measured a blood sugar level of 205 at 8:02 on Dec. 1, 2000, compared to a threshold value of 200".

Embodiment 2

In the above described Embodiment 1, all the information is placed only in the server 2. In this case, management is simplified but a network connection must be established each time action must be taken. Consequently, there is a redundant time loss of about one minute between a call between computers and the establishment of the network, and frequent actions may degrade performance. This will not be a problem if constantly connected WANs 4 are generalized in the future, but the degraded performance currently poses a problem because modem connections with analog telephone lines are generally used.

To prevent the degraded performance, this embodiment transmits all actions, for example, power-on and off and measuring times for each sensor from the server 2 to the client 1 beforehand as schedule information and stores this information in the client 1. The contents of an action plan are the same as those in (Table 1).

The client 1 can detect times while sleeping. At set points of time, the client 1 starts up automatically to enter a normal state, while displaying a message such as a greeting. First, the client 1 is automatically connected to the server 2 to check whether or not the schedule has been changed. More specifically, when the client 1 is connected to the server 2, it searches the server 2 for its own schedule to check the date when the schedule was prepared. If a schedule is present which has been created later than the one possessed by the client 1, the client 1 automatically loads it to update the schedule to the latest.

The client 1 subsequently performs operations such as warnings of scheduled measurements, data transfers, and power-off based on the descriptions in the schedule.

In this case, as described in Embodiment 1, the client 1 also compares the schedule possessed thereby with the results of measurements from the sensors. When the measurements were made ahead of the schedule and if the difference in time is smaller than the allowable value, the results are considered to be formal and the patient is not warned of the measuring time. If the difference in time is larger than the allowable value, the results are neglected because they are out of the scheduled range.

The present invention is media carrying programs and/or data for allowing a computer to execute all or some of the functions of all or some of the above described means or devices according to the present invention, the programs and/or data being readable by the computer and being read to execute the functions in cooperation with the computer.

The data include data themselves as well as data structures, data formats, and data types.

The media include recording media such as ROMs, transmission media such as the Internet, and transmission media such as optical, electric, and acoustic waves.

The carrying media include, for example, recording media having the program/data recorded thereon, transmission media for transmitting the program/data, and the like.

The expression "the media can be processed by the computer" means that the recording media such as ROMs can be read by the computer or the transmission media can be handled by the computer as a result of a transmission.

The information assembly includes, for example, software such as programs and/or data.

As described above, the configuration of the present invention may be implemented using software or hardware.

As described above, the present invention enables the entire medical information system connecting a patient's home and a remote practitioner together via a network to systematically function as an entire system to provide society with efficient medical treatments as have not been realized by the prior art.

What is claimed is:

1. In a network including a plurality of patient terminals and a server terminal, a method of communicating medical information comprising the steps of:
   (a) storing only in the server terminal, a schedule showing a desired time for measuring at least one of a plurality of parameters indicating health of each patient;
   (b) transmitting and identifying from the server terminal to a respective patient terminal a parameter, based on the schedule stored only in the server, to be measured at a respective patient terminal;
   (c) measuring the parameter identified in step (b) at the respective patient terminal;
   (d) repeating steps (b) and (c) in turn for each of the other respective parameters, based on the schedule to be measured stored only in the server terminal; and
   (e) transmitting from each respective patient terminal to the server terminal the measured parameters, after measuring in step (c).

2. The method of claim 1, including the steps of:
   comparing, at the server terminal, a value of the measured parameter to a predetermined range of values stored in the server terminal, after step (e); and
   transmitting, from the server terminal to an administrator terminal, the measured parameter, if the value of the measured parameter is not within the predetermined range of values.

3. In a network including a plurality of patient terminals and a server terminal, a method of communicating medical information comprising the steps of:
   (a) storing only in the server terminal, a schedule showing a desired time for measuring at least one of a plurality of parameters indicating health of each patient;
   (b) transmitting and identifying from the server terminal to a respective patient terminal a parameter, based on the schedule stored only in the server terminal to be measured at a respective patient terminal;
   (c) measuring the parameter identified in step (b) at the respective patient terminal;
   (d) transmitting, from the respective patient terminal to the server terminal, the measured parameter, after measuring in step (c); and
   (e) repeating steps (b)–(d) for each of the other respective parameters based on the schedule to be measured stored only in the server terminal.

4. The method of claim 3 including the steps of:
   comparing, at the server terminal, a value of the measured parameter to a predetermined range of values stored in the server terminal, after step (e); and
   transmitting, from the sever terminal to an administrator terminal, the measured parameter, if the value of the measured parameter is not within the predetermined range of values.

5. In a network including a plurality of patient terminals and a server terminal, a method of communicating medical information comprising the steps of:
   (a) storing in the server terminal, a schedule showing a desired time for measuring at least one of a plurality of parameters indicating health of each patient;
   (b) transmitting and identifying from the server terminal to a respective patient terminal a parameter, based on the schedule stored in the server terminal, to be measured at a respective patient terminal;
   (c) determining only by the server terminal that the respective patient terminal has not made the measurement of step (b); and
   (d) transmitting by the server terminal to the respective patient terminal a predetermined alarm signal, if the server terminal makes the determination of step (c).

6. In a network including a plurality of patient terminals and a server terminal, a method of communicating medical information comprising the steps of:

(a) storing in the server terminal, a schedule showing a desired time for measuring at least one of a plurality of parameters indicating health of each patient;

(b) measuring a parameter of step (a) of a respective patient at a respective patient terminal at a time determined by the respective patient;

(c) transmitting by the respective patient terminal to the server terminal the parameter measured in step (b);

(d) receiving by the server terminal the parameter transmitted in step (c); and (e) comparing the parameter received in step (d) by the server terminal measured at the time determined in step (b) with the schedule of desired times in step (a); and (f) accepting by the server terminal the measurement of step (b) if the time comparison of step (e) is less than a predetermined time.

7. The method of claim 6 including the steps of:

(g) transmitting and identifying from the server terminal to a respective patient terminal a parameter based on the schedule stored in the server terminal in step (a) to be measured at a respective patient terminal; and (h) stopping the transmission to the respective patient terminal in step (g) of the parameter compared and accepted in steps (e) and (f).

8. A medical information system comprising a plurality of patient terminals and a server terminal configured to communicate in a network, the server terminal including a stored schedule showing a desired time for measuring each one of a plurality of parameters indicating health of each patient, the schedule stored only in the server terminal, the server terminal including a transmitter for transmitting, from the server terminal to a respective patient terminal, each parameter identified by the server terminal to be measured at a respective patient terminal, based on the schedule stored only in the server terminal, the respective patient terminal configured to (1) measure each parameter identified by the server terminal and (2) store each measured parameter based on the schedule, and the respective patient terminal including a transmitter for transmitting to the server terminal the stored measured parameters.

9. A medical information system comprising a plurality of patient terminals and a server terminal configured to communicate in a network, the server terminal including a stored schedule showing a desired time for measuring at least one of a plurality of parameters indicating health of each patient, the schedule stored only in the server terminal, the server terminal including a transmitter for transmitting, from the server terminal to a respective patient terminal, the parameter identified by the server terminal to be measured at a respective patient terminal, based on the schedule stored only in the server terminal, the respective patient terminal configured to measure the parameter identified by the server terminal, and the respective patient terminal including a transmitter for transmitting to the server terminal the measured parameter.

10. A medical information system comprising a plurality of patient terminals and a server terminal configured to communicate in a network, the server terminal including a stored schedule showing a desired time for measuring at least one of a plurality of parameters indicating health of each patient, the server terminal including a transmitter for transmitting, from the server terminal to a respective patient terminal, the at least one parameter identified by the server terminal to be measured at a respective patient terminal, based on the schedule stored in the server terminal, the server terminal configured to determine that the respective patient terminal has not made a measurement of the at least one parameter identified by the server terminal, and the server terminal including a predetermined alarm signal, wherein the predetermined alarm signal is transmitted to the respective patient terminal, if the server terminal determines that the measurement has not been made.

11. A medical information system comprising a plurality of patient terminals and a server terminal configured to communicate in a network, the server terminal including a stored schedule showing a desired time for measuring at least one of a plurality of parameters indicating health of each patient, the patient terminal configured to receive a measurement of a parameter, the parameter measured of a respective patient at a time determined by the respective patient, the respective patient terminal including a transmitter for transmitting, to the server terminal, the measurement of the parameter of the respective patient, the server terminal including a receiver for receiving the measurement of the parameter of the respective patient, and a comparator for comparing the time determined by the respective patient and a desired time of measurement in the stored schedule, and the server terminal configured to accept the received measurement performed by the respective patient, if the time comparison performed by the server terminal is less than a predetermined time.

12. The medical information system according to anyone of claims 8–11, wherein said server terminal has a function for managing information unique to a user using said patient terminal and can supply individual data or individual control information to said patient terminal based on the information unique to said user.

13. The medical information system according to anyone of claims 8–11, including sensors for measuring the parameters, said sensors including at least one of a clinical thermometer, a hemadynamometer, a pulsimeter, a blood sugar level meter, a saturated blood oxygen densitometer, scales, a fat meter, a stethoscope, an electrocardiograph, a still imaging device, an animation imaging device and a spirometer.

14. The medical information system according to anyone of claims 8–11, wherein said server terminal includes threshold values for data that depend on a condition of each patient's health and has a function for transmitting a signal to an administrator terminal via the network when the measured data transferred from said patient terminal deviates from said threshold values.

15. The medical information system according to anyone of claims 8–11, wherein said patient terminal includes threshold values for data that depend on the condition of each patient's health and has a function for transmitting a signal to an administrator terminal via the network when the measured data transferred from said patient terminal deviates from said threshold values.

16. The medical information system according to anyone of claims 8–11, wherein said server terminal stores at least part of software driving said patient terminal or/and an administrator terminal and has a function operating when said software is updated, to automatically update said software in said patient terminal or/and said administrator terminal.

* * * * *